(12) United States Patent
Branch

(10) Patent No.: US 9,217,683 B2
(45) Date of Patent: Dec. 22, 2015

(54) IMPACT INDICATOR

(71) Applicant: ShockWatch, Inc., Dallas, TX (US)

(72) Inventor: Clinton A. Branch, Jacksboro, TX (US)

(73) Assignee: ShockWatch, Inc., Dallas, TX (US)

( * ) Notice: Subject to any disclaimer, the term of this patent is extended or adjusted under 35 U.S.C. 154(b) by 390 days.

(21) Appl. No.: 13/900,690

(22) Filed: May 23, 2013

(65) Prior Publication Data

US 2013/0247814 A1 Sep. 26, 2013

Related U.S. Application Data

(63) Continuation of application No. 13/554,106, filed on Jul. 20, 2012, now Pat. No. 8,646,401, which is a continuation of application No. 13/415,961, filed on Mar. 9, 2012, now Pat. No. 8,234,994.

(60) Provisional application No. 61/451,143, filed on Mar. 10, 2011.

(51) Int. Cl.
*G01L 5/00* (2006.01)
*H01H 35/14* (2006.01)
(Continued)

(52) U.S. Cl.
CPC .............. *G01L 5/0052* (2013.01); *G01P 15/036* (2013.01); *H01H 35/14* (2013.01);
(Continued)

(58) Field of Classification Search
CPC ......... G01P 15/00; G01P 15/02; G01P 15/03; G01P 15/04; G01P 15/036; G01L 5/00; G01L 23/00; G01L 5/0052; G01N 3/30; H01H 35/14; H01H 9/16

USPC .............. 116/200, 201, 203, 211, 212, 215; 73/12.01, 12.04, 12.05, 12.06, 12.09, 73/12.13

See application file for complete search history.

(56) References Cited

U.S. PATENT DOCUMENTS 2,825,297 A 3/1958 Harrison
2,976,732 A 3/1961 Hautly
(Continued)

FOREIGN PATENT DOCUMENTS

DE 19754653 9/1999
GB 826735 1/1960
(Continued)

OTHER PUBLICATIONS

European Search Report; European Patent Application No. 12754873.3; Jul. 11, 2014.
(Continued)

*Primary Examiner* — R. A. Smith
*Assistant Examiner* — Tania Courson
(74) *Attorney, Agent, or Firm* — James L. Baudino

(57) ABSTRACT

A device and technique for impact detection and indication includes a housing; a mass member located within the housing, the housing configured to enable movement of the mass member from a first position to a second position within the housing in response to receipt by the housing of an acceleration event; and first and second biasing members disposed within the housing and biased toward each other to retain the mass member in the first position. In response to receipt by the housing of the acceleration event, the mass member is configured to overcome the biasing force of the first biasing member and move from the first position to the second position, and wherein the first and second biasing members each comprises a leaf spring member having a length greater than a width of the mass member and disposed transversely to a direction of movement of the mass member.

20 Claims, 10 Drawing Sheets

(51) Int. Cl.
  *G01P 15/04* (2006.01)
  *G01P 15/03* (2006.01)
  *G01P 15/02* (2013.01)
  *G01P 15/00* (2006.01)
  *G01L 23/00* (2006.01)
  *G01N 3/30* (2006.01)
  *H01H 9/16* (2006.01)

(52) U.S. Cl.
  CPC    *G01L 5/00* (2013.01); *G01L 23/00* (2013.01); *G01N 3/30* (2013.01); *G01P 15/00* (2013.01); *G01P 15/02* (2013.01); *G01P 15/03* (2013.01); *G01P 15/04* (2013.01); *H01H 9/16* (2013.01)

(56)                References Cited

U.S. PATENT DOCUMENTS

| | | | |
|---|---|---|---|
| 3,021,813 A | 2/1962 | Rips | |
| 3,312,188 A | 4/1967 | Lode et al. | |
| 3,373,716 A | 3/1968 | Williams | |
| 3,461,730 A | 8/1969 | Peters | |
| 3,623,449 A | 11/1971 | Knutson | |
| 3,707,722 A | 12/1972 | Itoh | |
| 3,782,204 A | 1/1974 | Boardman | |
| 3,835,809 A | 9/1974 | Sinn, Jr. | |
| 3,909,568 A | 9/1975 | Greenhug | |
| 4,060,004 A | 11/1977 | Scholz et al. | |
| 4,068,613 A | 1/1978 | Rubey | |
| 4,103,640 A * | 8/1978 | Feder | 116/210 |
| 4,125,085 A | 11/1978 | Rubey | |
| 4,177,751 A | 12/1979 | Rubey | |
| 4,237,736 A | 12/1980 | Wright | |
| 4,361,106 A | 11/1982 | Eklof | |
| 4,470,302 A | 9/1984 | Carte | |
| 4,688,244 A | 8/1987 | Hannon et al. | |
| 4,982,684 A | 1/1991 | Rubey | |
| 5,027,105 A | 6/1991 | Dailey et al. | |
| 5,051,725 A | 9/1991 | Caccitolo | |
| 5,153,561 A | 10/1992 | Johnson | |
| 5,269,252 A | 12/1993 | Nagai | |
| 5,347,274 A | 9/1994 | Hassett | |
| 5,551,279 A * | 9/1996 | Quick | 73/12.01 |
| 5,962,789 A | 10/1999 | Matsunaga et al. | |
| 6,272,901 B1 | 8/2001 | Takeuchi et al. | |
| 6,685,094 B2 | 2/2004 | Cameron | |
| 6,848,389 B1 | 2/2005 | Elsasser et al. | |
| 7,119,759 B2 | 10/2006 | Zehner et al. | |
| 7,219,619 B2 | 5/2007 | Fitzer et al. | |
| 7,353,615 B1 | 4/2008 | Branch | |
| 7,509,835 B2 | 3/2009 | Beck | |
| 8,074,489 B2 | 12/2011 | Ishikawa et al. | |
| 8,234,993 B2 | 8/2012 | Naruishi et al. | |
| 8,240,270 B2 | 8/2012 | Naruishi | |
| 8,307,775 B2 | 11/2012 | Naruishi et al. | |
| 8,616,146 B2 * | 12/2013 | Martin et al. | 116/203 |
| 2004/0231428 A1 | 11/2004 | Roberge | |
| 2005/0039669 A1 | 2/2005 | Elsasser et al. | |
| 2007/0194943 A1 | 8/2007 | Fitzer et al. | |
| 2009/0307827 A1 | 12/2009 | Aspray | |

FOREIGN PATENT DOCUMENTS

| | | |
|---|---|---|
| GB | 1409847 | 10/1975 |
| JP | S36-28494 | 10/1961 |
| JP | S57-142363 | 9/1982 |
| JP | 2009156726 | 7/2009 |

OTHER PUBLICATIONS

Official Notification of Substantive Examination; China Patent Application 201280009729.4 filed Aug. 21, 2013 (priority to PCT Application No. PCT/US2012/028423 filed Mar. 9, 2012); May 6, 2014.

International Search Report and Written Opinion; International Application No. PCT/US2012/028423; 9 pages.

Notification from Japan Patent Office; Japan Application No. 2013-557891; Sep. 5, 2014.

\* cited by examiner

IMPACT INDICATOR

BACKGROUND

During manufacturing, storage or transit, many types of objects need to be monitored due to the sensitivity or fragility of the objects. For example, some types of objects may be susceptible to damage if dropped or a significant impact is received. Thus, for quality control purposes and/or the general monitoring of transportation conditions, it is desirable to determine and/or verify the environmental conditions to which the object has been exposed.

BRIEF SUMMARY

According to one aspect of the present disclosure, a device and technique for impact detection is disclosed. The impact indicator includes a housing; a mass member located within the housing, the housing configured to enable movement of the mass member from a first position to a second position within the housing in response to receipt by the housing of an acceleration event; and first and second biasing members disposed within the housing and biased toward each other to retain the mass member in the first position. In response to receipt by the housing of the acceleration event, the mass member is configured to overcome the biasing force of the first biasing member and move from the first position to the second position, and wherein the first and second biasing members each comprises a leaf spring member having a length greater than a width of the mass member and disposed transversely to a direction of movement of the mass member.

According to another embodiment of the present disclosure, an impact indicator includes a housing; a mass member located within the housing, the housing configured to enable movement of the mass member from a first position to a second position within the housing in response to receipt by the housing of an acceleration event; and first and second biasing members disposed within the housing and biased toward each other to retain the mass member in the first position. In response to receipt by the housing of the acceleration event, the mass member is configured to overcome the biasing force of the first biasing member and move from the first position to the second position. The housing comprises a plurality of sidewalls forming a translation path for movement of the mass member from the first position to the second position, and wherein each end of the first and second biasing members is disposed in a respective seat located in the sidewalls when the mass member is in the first position.

According to yet another embodiment of the present disclosure, an impact indicator includes a housing; a mass member located within the housing, the housing configured to enable movement of the mass member from a first position to a second position within the housing in response to receipt by the housing of an acceleration event; and first and second biasing members disposed within the housing and biased toward each other to retain the mass member in the first position. In response to receipt by the housing of the acceleration event, the mass member is configured to overcome the biasing force of the first biasing member and move from the first position to the second position. In response to receipt by the housing of the acceleration event, the first and second biasing members are biased in a same direction to bear upon the mass member to retain the mass member in the second position. In response to receipt by the housing of another acceleration event that causes the mass member to overcome the bias of the first and second biasing members, the first and second biasing members are configured to cause the mass member to move from the second position, past the first position, to a third position.

BRIEF DESCRIPTION OF THE SEVERAL VIEWS OF THE DRAWINGS

For a more complete understanding of the present application, the objects and advantages thereof, reference is now made to the following descriptions taken in conjunction with the accompanying drawings, in which.

DETAILED DESCRIPTION

Embodiments of the present disclosure provide a device and technique for impact detection and indication. According to one embodiment, an impact indicator includes a housing; a mass member located within the housing, the housing configured to enable movement of the mass member from a first position to a second position within the housing in response to receipt by the housing of an acceleration event; and first and second biasing members disposed within the housing and biased toward each other to retain the mass member in the first position. In response to receipt by the housing of the acceleration event, the mass member is configured to overcome the biasing force of the first biasing member and move from the first position to the second position, and wherein the first and second biasing members each comprises a leaf spring member having a length greater than a width of the mass member and disposed transversely to a direction of movement of the mass member. Embodiments of the present disclosure enable impact and/or acceleration event detection while preventing or substantially preventing a re-setting of the state of the impact indicator once a predetermined level or magnitude of impact has occurred. For example, in some embodiments, the mass member of the indicator is configured to move from a non-activated position to an activated position in response to an acceleration event. If the indicator receives an acceleration event that may be performed in an attempt to re-set indicator to the non-activated state (e.g., a level or magnitude sufficient to cause a reverse movement of mass member), the mass member moves from one activated position to another activated position.

Figure 1A:
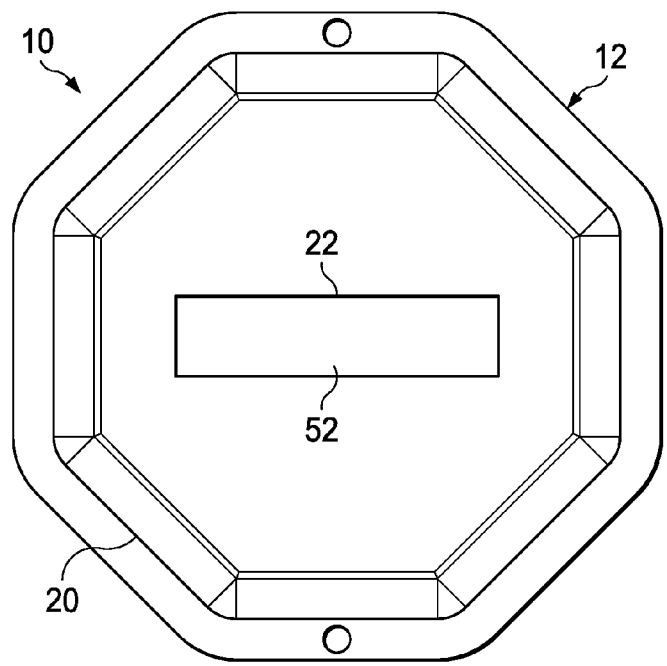
FIGS. 1A and 1B are diagrams illustrating respective front and rear views of an embodiment of an impact indicator according to the present disclosure.
Figure 1B:
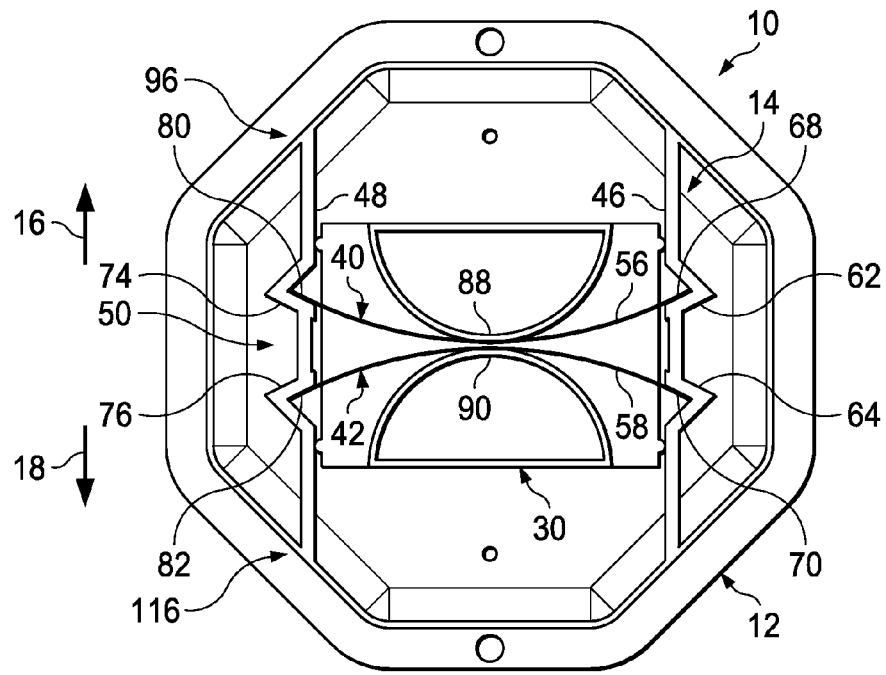

With reference now to the Figures and in particular with reference to FIGS. 1A and 1B, exemplary diagrams of an impact indicator 10 are provided in which illustrative embodiments of the present disclosure may be implemented. FIG. 1A is a diagram illustrating a front view of impact indicator 10, and FIG. 1B is a diagram illustrating a rear view of impact indicator 10. In FIGS. 1A and 1B, indicator 10 is a portable device configured to be affixed to or disposed within a transport container containing an object of which impact and/or acceleration events associated therewith are to be monitored. Embodiments of impact indicator 10 monitor whether an object has been exposed to an impact or some level of an acceleration event during manufacturing, storage and/or transport of the object. In some embodiments, impact indicator 10 may be affixed to a transport container using, for example, adhesive materials, permanent or temporary fasteners, or a variety of different types of attachment devices. The transport container may include a container in which a monitored object is loosely placed or may comprise a container of the monitored object itself. It should be appreciated that FIGS. 1A and 1B are only exemplary and are not intended to assert or imply any limitation with regard to the environments in which different embodiments may be implemented.

In the embodiment illustrated in FIGS. 1A and 1B, impact indicator 10 comprises a housing 12 having a detection assembly 14 disposed therein. In the illustrated embodiment, detection assembly 14 is configured to detect and indicate impact or acceleration events in either of two different directions, indicated by direction 16 or direction 18 relative to indicator 10 in FIG. 1B (i.e., in direction 16/18 or at an angle thereto having a directional vector component in a corresponding direction 16/18). However, it should be understood that assembly 14 may be configured for detecting/indicating an impact event corresponding to a single direction (as will be described further below). Further, it should be understood that additional detection assemblies 14 may be included in indicator 10 to provide impact detection/indication in additional directions.

In some embodiments, housing 12 is configured and/or constructed from a clear or semi-opaque material having a masking label 20 located on a front side thereof or affixed thereto (FIG. 1A). In some embodiments, masking label 20 is configured having one or more apertures or "windows" 22 for providing a visual indication of impact detection. For example, as will be described further below, in response to indicator 10 being subjected to or receiving some predetermined level of impact or acceleration event, detection assembly 14 causes a visual indication to be displayed within or through one or more of windows 22 to provide a visual indication that the monitored object has or may have been subjected to some level of impact. However, it should be understood that other methods may be used to provide a visual indication that detection assembly 14 has moved and/or been otherwise placed into an activated state indicating that indicator 10 has experienced a shock, impact or acceleration event. It should also be understood that housing 12 may be configured and/or manufactured from other materials (e.g., opaque materials having one or more windows 22 formed therein).

Referring to FIG. 1B, detection assembly 14 is illustrated in a non-activated or initial pre-detection state (i.e., prior to being subjected to an acceleration event). In the illustrated embodiment, detection assembly 14 comprises a weight or mass member 30 and spring members 40 and 42. Housing 12 comprises sidewalls 46 and 48 located on opposite sides of mass member 30. Sidewalls 46 and 48 form a translation path to enable movement of mass member 30 within housing 12 in response to housing 12 or indicator 10 being subjected to an acceleration event. For example, in FIG. 1B, mass member 30 is located in a non-activated position 50 within housing 12. Additionally, referring to FIG. 1A, a medial surface portion 52 of mass member 30 is located within and/or is otherwise visible within window 22.

In the embodiment illustrated in FIG. 1B, spring members 40 and 42 bias mass member 30 to the non-activated position 50 in the pre-detection state of indicator 10. For example, in the illustrated embodiment, spring members 40 and 42 comprises leaf springs 56 and 58, respectively; however, it should be understood that other types of biasing elements may be used. In FIG. 1B, sidewall 46 has formed therein recesses or seats 62 and 64 for holding respective ends 68 and 70 of leaf springs 56 and 58. Sidewall 48 has formed therein recesses or seats 74 and 76 for holding respective ends 80 and 82 of leaf springs 56 and 58. Leaf springs 56 and 58 are formed having a length greater than a width of mass member 30 (e.g., as measured in a direction from sidewall 46 to sidewall 48). The ends 68 and 80 of leaf spring 56 are located in respective seats 62 and 74 such that leaf spring 56 is positioned in an orientation transverse to the movement path of mass member 30. The ends 70 and 82 of leaf spring 58 are located in respective seats 64 and 76 such that leaf spring 58 is positioned in an orientation transverse to the movement path of mass member 30. For example, the translation path formed by sidewalls 46 and 48 enables movement of mass member 30 in the directions indicated by 16 and 18.

Ends 68 and 80 of leaf spring 56 are located in seats 62 and 80, and ends 70 and 82 of leaf spring 58 are located in respective seats 64 and 76, such that leaf springs 56 and 58 have convex surfaces facing each other. Thus, in the illustrated embodiment, leaf springs 56 and 58 are biased towards each other. In the embodiment illustrated in FIG. 1B, leaf springs 56 and 58 each extend laterally across a medial portion of mass member 30 between opposing arcuately formed walls 88 and 90 of mass member 30. Leaf springs 56 and 58 are biased toward each other and support mass 30 in the non-activated position 50 (e.g., leaf springs 56 and 58 contact and support respective walls 88 and 90 of mass member 30 to retain mass member 30 in the non-activated position 50). It should be understood that mass member 30 may be otherwise formed and/or spring members 40 and 42 may be otherwise configured and/or positioned relative to mass member 30 to retain and/or bias mass member 30 to the non-activated position 50.

Figure 2A:
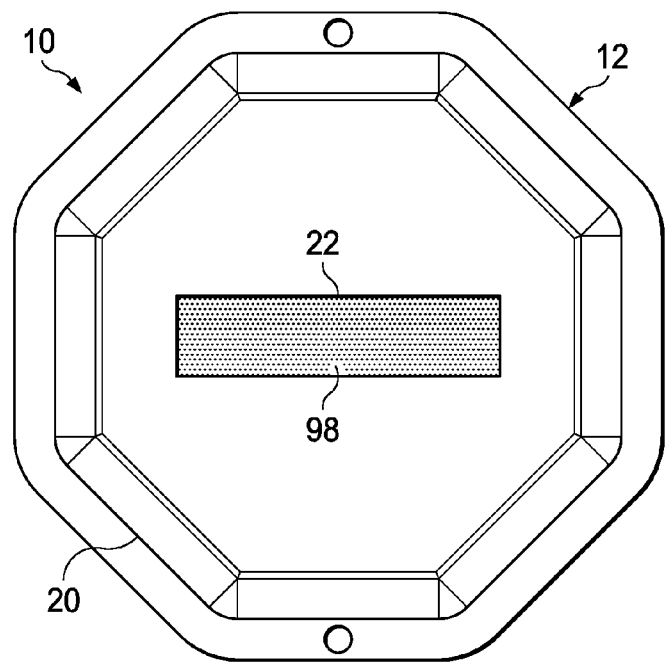
FIGS. 2A and 2B are diagrams illustrating respective front and rear views of the impact indicator of FIGS. 1A and 1B in an activated state according to the present disclosure.
Figure 2B:
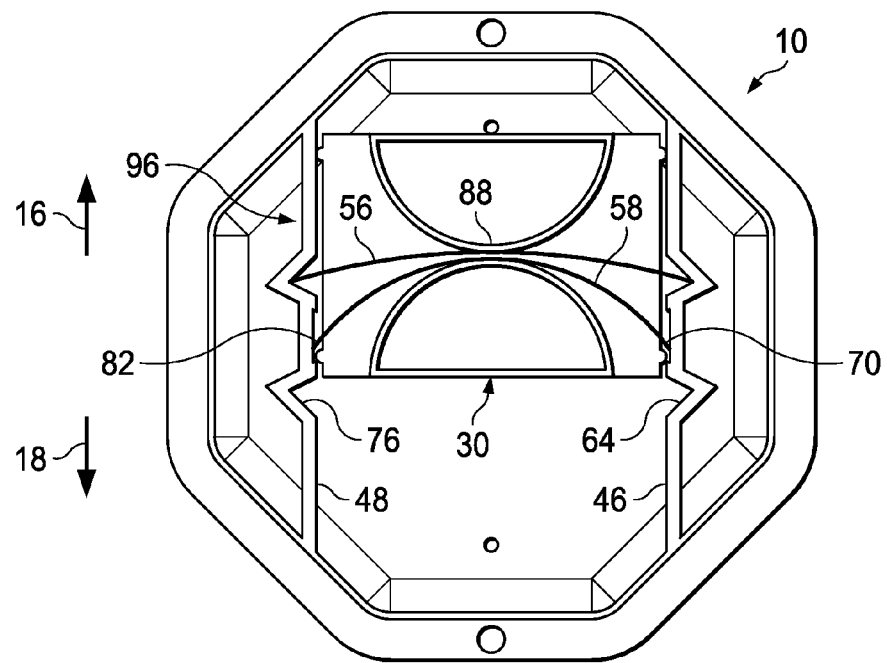

FIGS. 2A and 2B are diagrams illustrating respective front and rear views of indicator 10 illustrated in FIGS. 1A and 1B in an activated state. In the embodiment illustrated in FIGS. 2A and 2B, indicator 10 and/or housing 12 has been subjected to an impact and/or acceleration event in a direction corresponding to direction 16 of a level and/or magnitude to overcome the bias force of spring members 40 and 42 and thereby cause mass member 30 to move from non-activated position 50 to an activated position 96. In response to the acceleration event, leaf spring 56 inverts and a convex portion thereof applies a biasing force against wall 88 of mass member 30 to bias mass member 30 to the activated position 96. Additionally, in response to the acceleration event and movement of mass member 30 to the activated position 96, ends 70 and 82 of leaf spring 58 are drawn out of respective seats 64 and 76. As best illustrated in FIG. 2A, in the activated position 96, a different portion of mass member 30 is located within and/or is otherwise visible in window 22 than when mass member 30 is in the non-activated position 50. For example, in the non-activated position 50, a medial portion of mass member 30 (e.g., medial surface portion 52 (FIG. 1A)) is located within and/or is otherwise visible in window 22. However, in response to movement of mass member 30 to the activated position 96, a surface portion 98 located adjacent medial surface portion 52 is located within and/or is otherwise visible in window 22. As will be described further below, mass member 30 may contain, at different locations thereon, different types and/or forms of indicia on a side thereof facing window 22 corresponding to the non-activated and activated positions of mass member 30 within housing 12 to provide an indication as to whether indicator 10 has been subjected to a certain level or magnitude of acceleration event/impact.

Figure 3A:
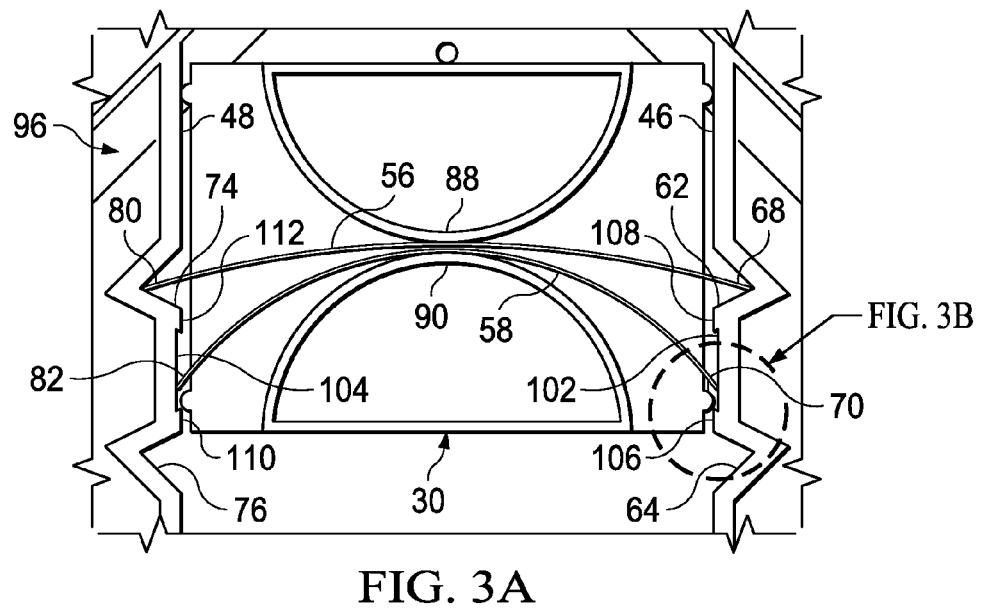
FIG. 3A is a diagram illustrating an enlarged view of a portion of the impact indicator illustrated in FIG. 2B in accordance with the present disclosure.
Figure 3B:
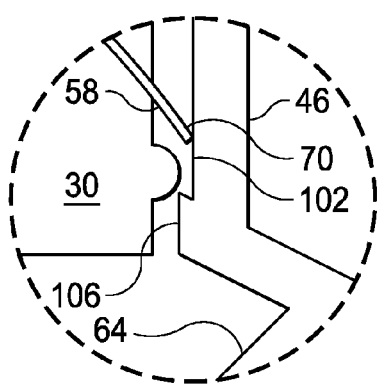
FIG. 3B is a diagram illustrating an enlarged view of a portion of the impact indicator illustrated in FIG. 3A in accordance with the present disclosure.

FIG. 3A is a diagram illustrating an enlarged view of a portion of FIG. 2B of indicator 10, and FIG. 3B is a diagram illustrating an enlarged view of a portion of FIG. 3A of indicator 10. Referring to FIGS. 2B, 3A and 3B, as described above, in response to an acceleration event in direction 16 of a level and/or magnitude to overcome the bias force of spring members 40 and 42, leaf spring 56 inverts and a convex portion thereof applies a biasing force against wall 88 of mass member 30 to bias mass member 30 to the activated position 96. Additionally, ends 70 and 82 of leaf spring 58 are drawn out of respective seats 64 and 76. As best illustrated in FIGS. 3A and 3B, sidewalls 46 and 48 have formed therein indent regions 102 and 104, respectively, that are set back and/or offset from adjacent wall surfaces 106, 108, 110 and 112 of sidewalls 46 and 48, respectively. Indent region 102 is located along sidewall 46 between seats 62 and 64, and indent regions 104 is located along sidewall 48 between seats 74 and 76. In response to movement of mass member 30 to the activated position 96, ends 70 and 82 of leaf spring 58 are drawn out of respective seats 64 and 76 and become positioned within respective indent regions 102 and 104. Indent regions 102 and 104 prevent or substantially prevent ends 70 and 82 of leaf spring 58 from returning to respective seats 64 and 76. Thus, if indicator 10 is subjected to another acceleration event in a direction opposite direction 16 (e.g., direction 18) in an attempt to reset and/or re-position mass member 30 in the non-activated position 50 after being in an activated state, indent regions 102 and 104 resist the return of ends 70 and 82 of leaf spring 58 to seats 64 and 76, thereby resulting in an additional bias force in the direction 16 that would need to be overcome in an opposite direction to effectuate movement of mass member 30 toward the non-activated position 50.

Figure 4A:
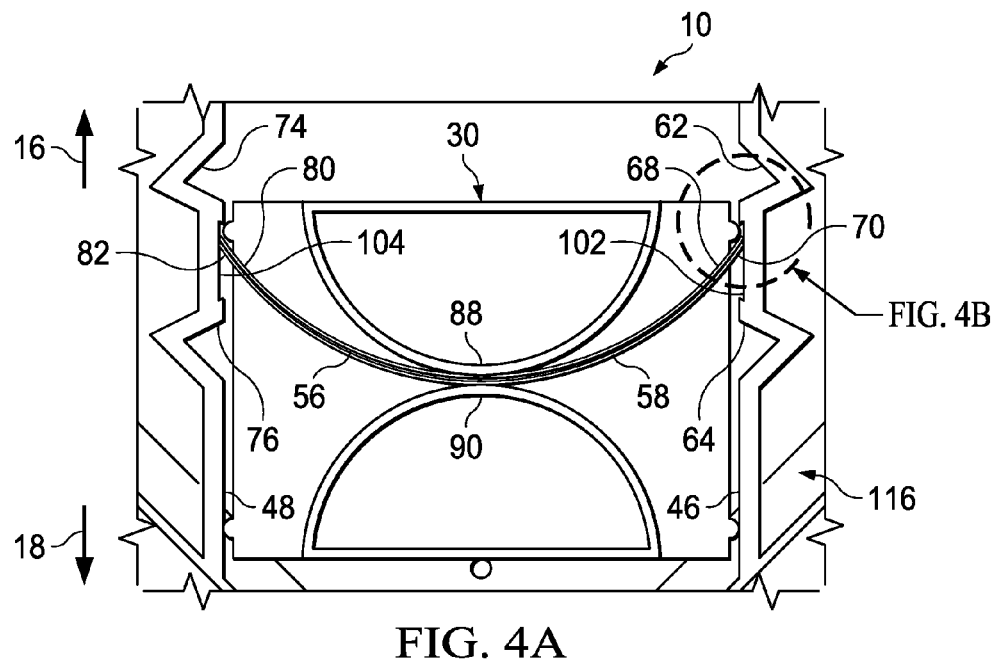
FIG. 4A is another diagram illustrating an enlarged view of a portion of the impact indicator of FIGS. 1A and 1B in an activated state according to the present disclosure.
Figure 4B:
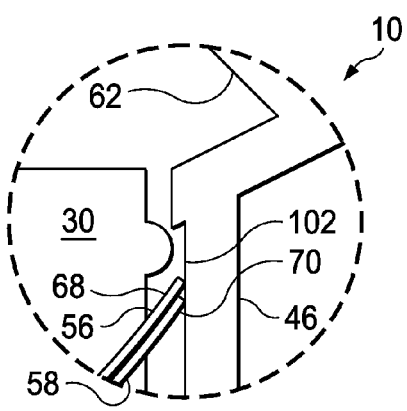
FIG. 4B is a diagram illustrating an enlarged view of a portion of the impact indicator illustrated in FIG. 4A in accordance with the present disclosure.

FIG. 4A is a diagram illustrating an enlarged view of a portion of indicator 10 with mass member 30 located in another activated position 116 (e.g., on a side of housing 12 opposite activated position 96), and FIG. 4B is a diagram illustrating an enlarged view of a portion of FIG. 4A. For clarity, referring to FIG. 1B, mass member 30 is depicted therein in non-activated position 50. Activated positions 96 and 116 are referenced in FIG. 1B to illustrate locations within housing 12 where mass member 30 will be located when in activated positions 96 and 116. Referring to FIGS. 4A and 4B, if indicator 10 has been subjected to an acceleration event in direction 16 that caused mass member 30 to move to activated position 96 (FIG. 2B) and thereafter is subjected to another acceleration event in direction 18 (e.g., an unauthorized attempt to reseat mass member 30 in the non-activated position 50 or in response to some other impact event) of a level and/or magnitude to overcome the force(s) applied by leaf springs 56 and 58, leaf springs 56 and 58 both collapse or invert and mass member 30 moves from activated position 96, past non-activated position 50, to the activated position 116. For example, in response to the acceleration event in direction 18 of a level and/or magnitude to overcome the force(s) applied by leaf springs 56 and 58, leaf springs 56 and 58 both collapse or invert such that convex portions thereof apply a biasing force against wall 90 of mass member 30 to bias mass member 30 to activated position 116. Additionally, ends 68 and 80 of leaf spring 56 are drawn out of respective seats 62 and 74 and become positioned within respective indent regions 102 and 104. Thus, in response to movement of mass member 30 from activated position 96 to activated position 116, leaf springs 56 and 58 are biased in a same direction (e.g., toward wall 90 of mass member 30) and ends 68, 70, 80 and 82 of respective leaf springs 56 and 58 are located within indent regions 102 and 104, respectively, to prevent or substantially prevent leaf springs 56 and 58 to returning to seat 62, 64, 74 or 76, thereby further preventing or substantially preventing mass member 30 from returning (in a maintained durational state) to non-activated position 50 after being in an activated state.

Figure 5A:
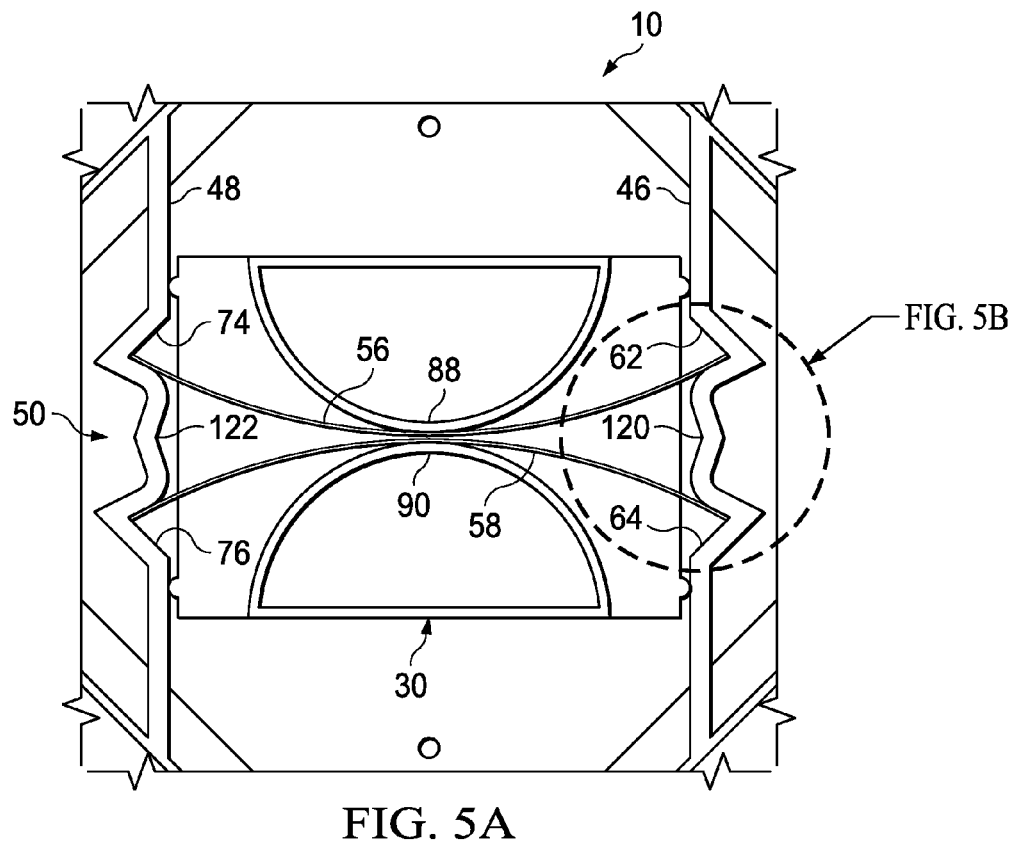
FIG. 5A is a diagram illustrating another embodiment of an impact indicator according to the present disclosure.
Figure 5B:
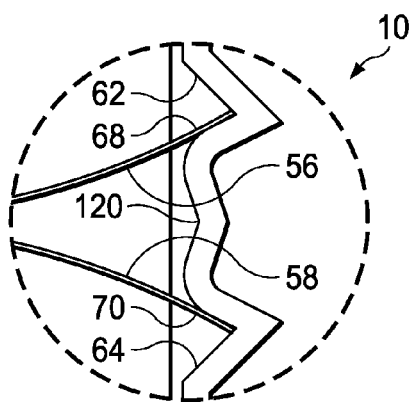
FIG. 5B is a diagram illustrating an enlarged view of a portion of the impact indicator illustrated in FIG. 5A in accordance with the present disclosure.
Figure 6:
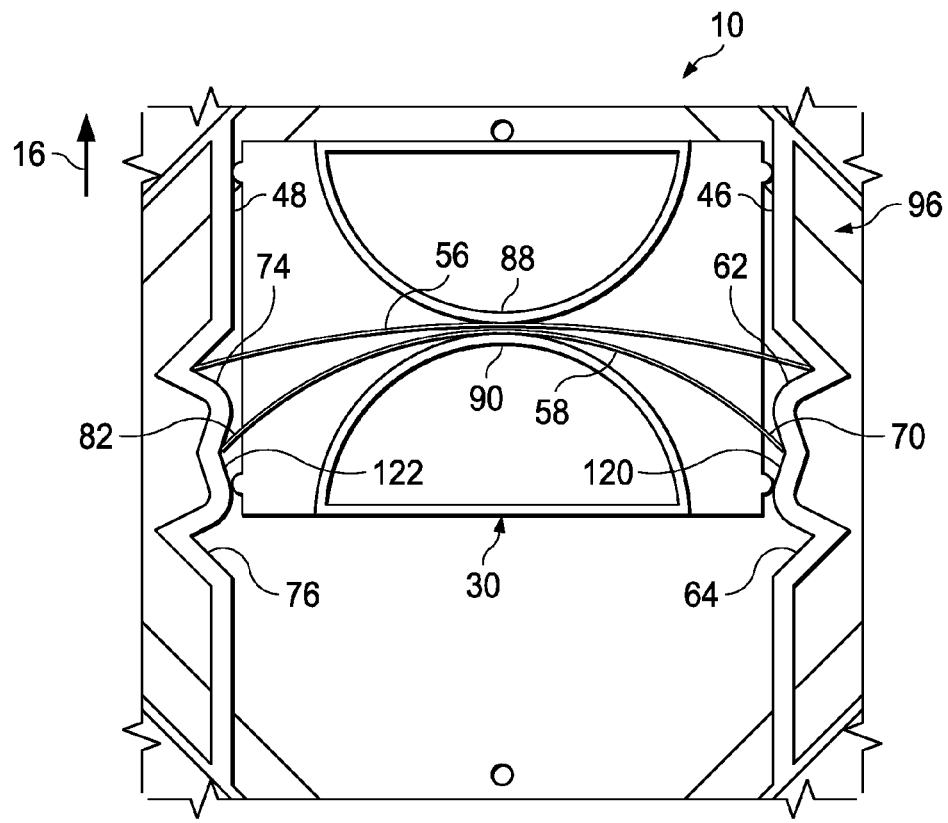
FIG. 6 is a diagram illustrating an enlarged view of a portion of the impact indicator illustrated in FIGS. 5A and 5B in an activated state in accordance with the present disclosure.

FIG. 5A is a diagram illustrating another embodiment of indicator 10 in accordance with the present disclosure, and FIG. 5B is a diagram illustrating an enlarged view of a portion of FIG. 5A of indicator 10. In the embodiment illustrated in FIGS. 5A and 5B, sidewalls 46 and 48 each have formed therein an additional spring seat 120 and 122, respectively. Seat 120 is located along sidewall 46 between seats 62 and 64, and seat 122 is located along sidewall 48 between seats 74 and 76. Similar to seats 62, 64, 74 and 76, seats 120 and 122 comprise a recessed area along respective sidewalls 46 and 48 for receiving ends 68/80 and 70/82 of respective leaf springs 56 and 58 in response to indicator 10 being subjected to an impact or acceleration event of sufficient magnitude to cause movement of mass member 30 (e.g., as described above in connection with FIGS. 2A, 3A, 3B, 4A and 4B). For example, FIG. 6 is a diagram illustrating indicator 10 shown in FIGS. 5A and 5B with mass member 30 located in the activated position 96. Because leaf springs 56 and 58 are configured having a length greater than a lateral width of the translation path for movement of mass member 30, the ends of leaf springs 56 and 58 will seek the widest lateral dimension between sidewalls 46 and 48 to relieve tension forces therein. Thus, for example, in response to indicator 10 being subjected to an acceleration event in direction 16 of a magnitude sufficient to overcome the bias forces of leaf springs 56 and 58, mass member 30 will move from non-activated position 50 toward activated position 96, leaf spring 56 will collapse and/or invert and apply a biasing force toward wall 88 of mass member 30, and ends 70 and 82 of leaf spring 58 will be drawn out of respective seats 64 and 76 and become located in respective seats 120 and 122. Seats 120 and 122 102 and 104 prevent or substantially prevent ends 70 and 82 of leaf spring 58 from returning to respective seats 64 and 76. Thus, if indicator 10 is subjected to another acceleration event in a direction opposite direction 16 (e.g., direction 18) in an attempt to reset and/or re-position mass member 30 in the non-activated position 50 after being in an activated state, indent regions 102 and 104 resist the return of ends 70 and 82 of leaf spring 58 to seats 64 and 76, thereby resulting in an additional bias force in the direction 16 that would need to be overcome in an opposite direction to effectuate movement of mass member 30 toward the non-activated position 50.

Figure 7A:
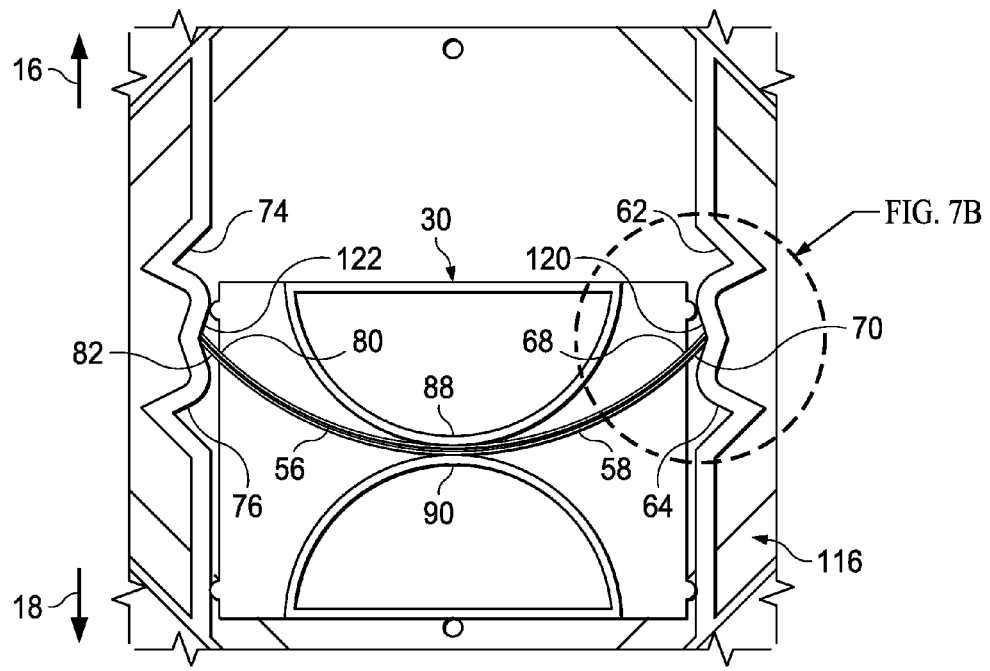
FIG. 7A is a diagram illustrating an enlarged view of a portion of the impact indicator illustrated in FIGS. 5A and 5B in another activated state in accordance with the present disclosure.
Figure 7B:
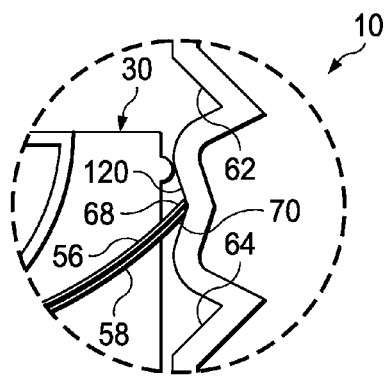
FIG. 7B is a diagram illustrating an enlarged view of a portion of the impact indicator illustrated in FIG. 7A in accordance with the present disclosure.

FIG. 7A is a diagram illustrating an enlarged view of a portion of indicator 10 of FIGS. 5A, 5B and 6 with mass member 30 located in activated position 116, and FIG. 7B is a diagram illustrating an enlarged view of a portion of FIG. 7A. If indicator 10 has been subjected to an acceleration event in direction 16 that caused mass member 30 to move to activated position 96 (FIG. 6) and thereafter is subjected to another acceleration event in direction 18 (e.g., an unauthorized attempt to reseat mass member 30 in the non-activated position 50 or in response to some other impact event) of a level and/or magnitude to overcome the force(s) applied by leaf springs 56 and 58, leaf springs 56 and 58 both collapse or invert and mass member 30 moves from activated position 96, past non-activated position 50, to the activated position 116. For example, in response to the acceleration event in direction 18 of a level and/or magnitude to overcome the force(s) applied by leaf springs 56 and 58, leaf springs 56 and 58 both collapse or invert such that convex portions thereof apply a biasing force against wall 90 of mass member 30 to bias mass member 30 to activated position 116. Additionally, ends 68 and 80 of leaf spring 56 are drawn out of respective seats 62 and 74 and become positioned within respective seats 120 and 122. Thus, in response to movement of mass member 30 from activated position 96 to activated position 116, leaf springs 56 and 58 are biased in a same direction (e.g., toward wall 90 of mass member 30) and ends 68, 70, 80 and 82 of respective leaf springs 56 and 58 are located within seats 120 and 122, respectively, to prevent or substantially prevent leaf springs 56 and 58 to returning to seat 62, 64, 74 or 76, thereby further preventing or substantially preventing mass member 30 from returning (in a maintained durational state) to non-activated position 50 after being in an activated state.

Figure 8:
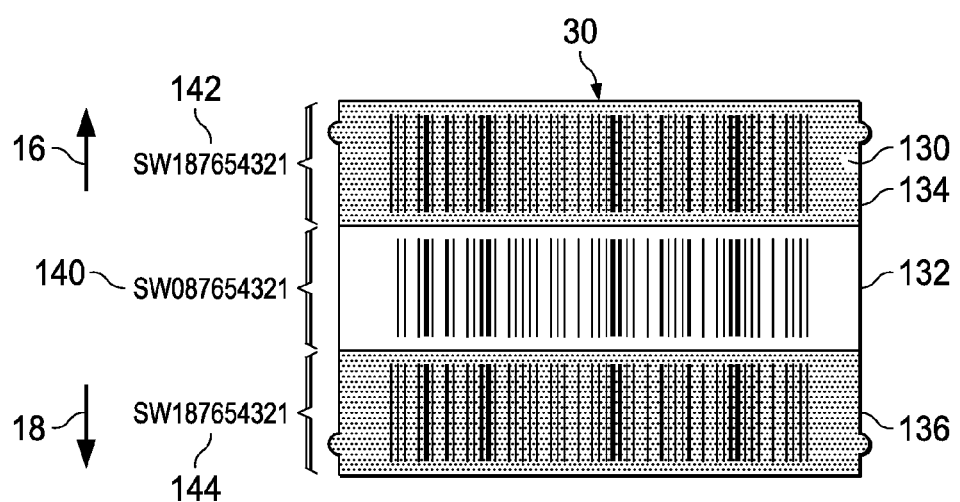
FIG. 8 is a diagram illustrating an embodiment of a mass member of the impact indictor illustrated in FIGS. 1A and 1B according to the present disclosure.

FIG. 8 is a diagram illustrating an embodiment of mass member 30 of indicator 10 in accordance with an embodiment of the present disclosure. In some embodiments, mass member 30 functions as a display element to indicate the activation status of indicator 10. For example, in FIG. 8, a surface 130 of mass member 30 facing outwardly through window 22 (FIG. 1A) is shown. In the illustrated embodiment, surface 130 comprises a non-activated surface portion 132 and activated surface portions 134 and 136. Each of surface portions 132, 134 and 136 may comprise different colors, marking or other types of indicia that are visually exposed through window 22 in either a non-activated or activated state of indicator 10. For example, non-activated surface portion 132 comprises a surface portion of mass member 30 that will be visible through window 22 when mass member 30 is located in the non-activated position 50. Activated surface portion 136 comprises a surface portion of mass member 30 that will be visible through window 22 when mass member 30 is located in the activated position 96 (e.g., FIGS. 2A and 2B), and activated surface portion 134 comprises a surface portion of mass member 30 that will be visible through window 22 when mass member 30 is located in the activated position 116 (e.g., FIGS. 4A and 4B). In some embodiments, surface portions 132, 134 and 136 comprise color codes to visually indicate whether indicator 10 is in a non-activated or activated state (i.e., an activated state indicating that indicator 10 has been subjected to some predetermined level or magnitude of impact or acceleration event). For example, surface portion 132 may comprise a white coloring, and surface portions 134 and 136 may comprise a red coloring. Thus, in a non-activated state, the white coloring of surface portion 132 would be visible within window 22. In an activated state (depending on the direction and/or quantity of acceleration events received), a red coloring corresponding to one of surface portions 134 or 136 would be visible through window 22. In this embodiment, a single window 22 is used as an example (e.g., a single window 22 placed in a position corresponding to the non-activated position 50 for mass member 30). However, it should be understood that different window quantities and/or placement may be used. For example, in some embodiments, two windows may be utilized each corresponding to an activated position of mass member 30 (e.g., one window located in a position corresponding to the activated position 96 for mass member 30, and another window located in a position corresponding to the activated position 116 of mass member 30). In this example, color coding of surface portions 134 and 136 may be omitted (e.g., color coding surface portion 132 a red color or other desired color that would be visible through either the window corresponding to activated position 96 or the activated position 116).

Figure 9A:
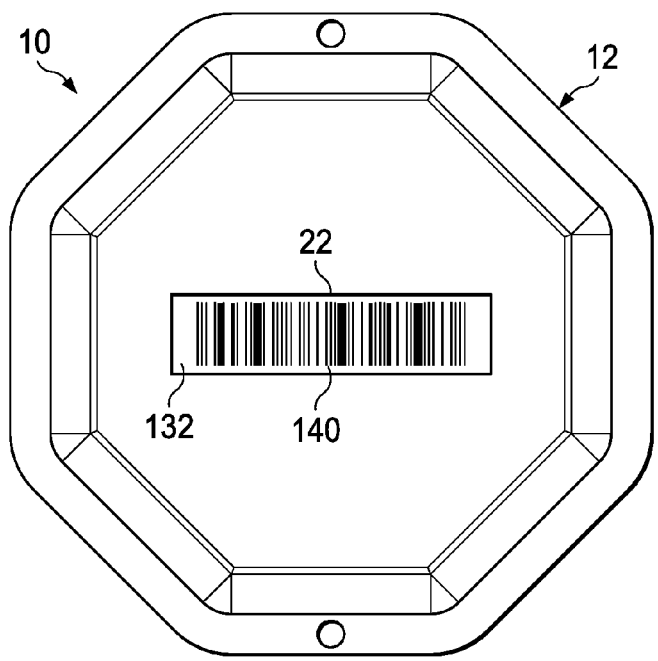
FIGS. 9A and 9B are diagrams illustrating respective non-activated and activated states of the impact indicator illustrated in FIGS. 1A and 1B with the mass member illustrated in FIG. 8 according to the present disclosure.
Figure 9B:
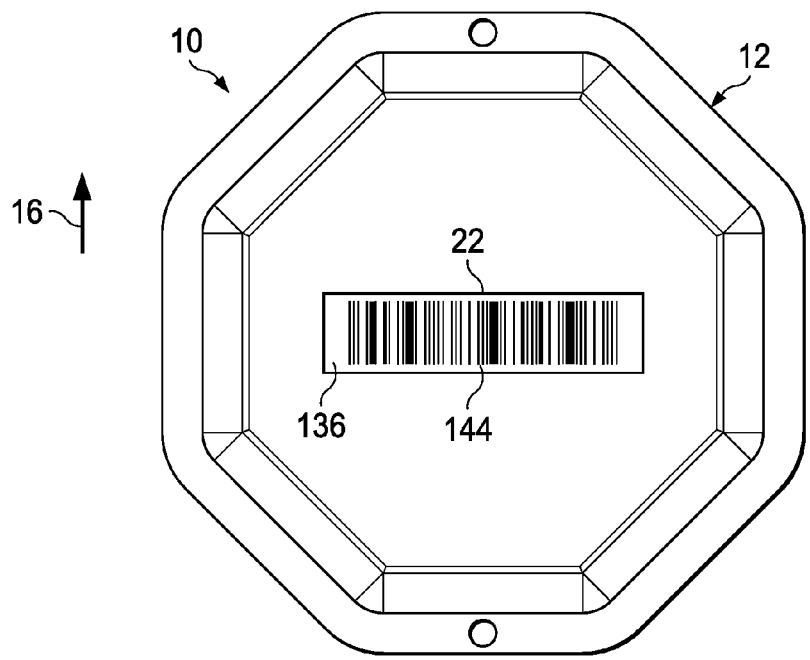

In the embodiment illustrated in FIG. 8, surface portions 132, 134 and/or 136 may comprise a barcode or other type of indicia (e.g., a numeric code, an alphanumeric code, or other type of encoded indicia, etc.) to indicate the activation or impact status of indicator 10 (e.g., a status identifier that may be encoded, machine-perceptible instead of human-perceptible, etc.). For example, in the illustrated embodiment, surface portion 132 includes a barcode indicia 140 representing the code/indicia of "SW087654321," and surface portions 134 and 136 include barcode indicia 142 and 144, respectively, representing the code/indicia of "SW187654321." In some embodiments, each of surface portions 132, 134 and 136 may comprise the same coloring (or the omission of different colors thereon). The barcode indicia 140, 142 and 144 may include information corresponding to manufacturer information, serial number information and status information. For example, in the illustrated embodiment, the first two characters/digits may be used to identify manufacturer or company information, the third character/digit may be used to indicate activation status, and the remaining characters/digits may be used to indicate serial number information. It should be understood that the various characters/digits of the barcode or other type of encoded indicia may be varied to represent different types of information. In some embodiments, the various characters/digits or other type of encoded indicia may be human-imperceptible and/or undecipherable as to the type and/or specific detail of the information represented by the encoded indicia. Thus, in this example, the third character/digit of "0" in indicia 140 indicates a non-activated status, while the third character/digit of "1" in indicia 142 and 144 indicates an activated status of indicator 10. FIGS. 9A and 9B are diagrams illustrating utilization of the barcode indicia 140, 142 and 144 for indicating activation status of indicator 10. Referring to FIGS. 8 and 9A, in a non-activated state (e.g., before being subjected to and/or experiencing some predetermined level or magnitude of impact/acceleration), indicia 140 is visible through window 22. Referring to FIGS. 8 and 9B, after receiving and/or being subject to some predetermined level or magnitude of impact/acceleration, indicia 142 or 144 would be visible through window 22. In the embodiment illustrated in FIG. 9B, in response to receipt of an acceleration event in the direction 16, for example, indicia 144 is visible within window 22.

Figure 10:
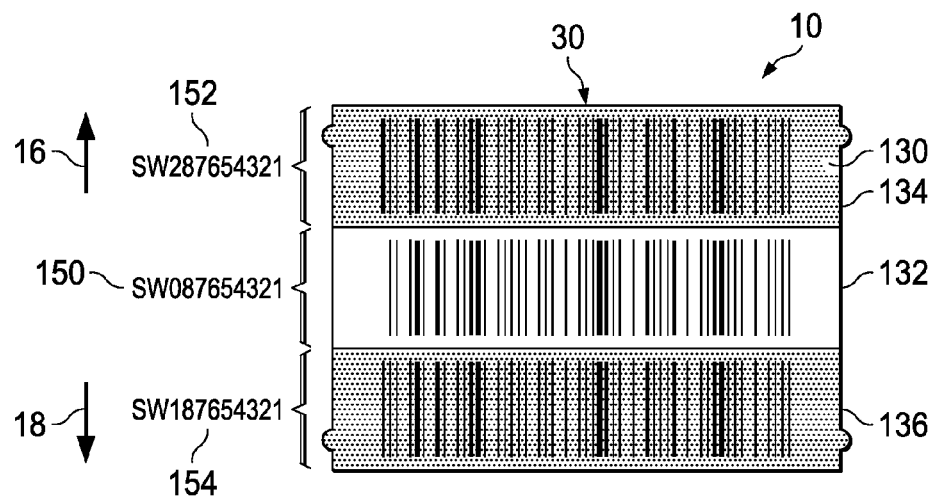
FIG. 10 is a diagram illustrating another embodiment of a mass member of the impact indictor illustrated in FIGS. 1A and 1B according to the present disclosure.

FIG. 10 is a diagram illustrating another embodiment of mass member 30 of indicator 10 in accordance with an embodiment of the present disclosure. In FIG. 10, surface 130 of mass member 30 facing outwardly through window 22 (FIG. 1A) is depicted. In the embodiment illustrated in FIG. 10, each of surface portions 132, 134 and 136 may comprise different colors, markings or other types of indicia that are visually exposed through window 22 to provide an indication of a direction of impact/acceleration in an activated state of indicator 10. For example, surface portion 132 may comprise a white coloring, surface portion 134 may comprise a yellow coloring, and surface portion 136 may comprise a red coloring. Thus, in a non-activated state, the white coloring of surface portion 132 would be visible within window 22. In an activated state, in response to receipt of some predetermined level or magnitude of impact/acceleration in the direction 16, the red coloring of surface portion 136 would be visible through window 22. In an activated state, in response to receipt of some predetermined level or magnitude of impact/acceleration in the direction 18, the yellow coloring of surface portion 134 would be visible through window 22. Thus, in the illustrated embodiment, mass member 30 functions as a display element for indicating an activation state of indicator 10 and/or a direction of impact if received. Therefore, indicator 10 may be configured to indicate an impact event as well as a direction of that impact event.

As illustrated in FIG. 10, surface portions 132, 134 and 136 may also include barcode or other type of encoded indicia for indicating a direction of an impact event (e.g., a status and/or directional identifier that may be encoded, machine-perceptible/machine-decipherable instead of human-perceptible/human-decipherable, etc.). For example, in the illustrated embodiment, surface portion 132 includes a barcode indicia 150 representing the code/indicia of "SW087654321," surface portion 134 includes barcode indicia 152 representing the code/indicia of "SW287654321," and surface portion 136 includes barcode indicia 154 representing the code/indicia of "SW187654321." In some embodiments, each of surface portions 132, 134 and 136 may comprise the same coloring (or the omission of different colors thereon). In this embodiment, the third character/digit is used to indicate a status of activation and, if activated, a direction of the received impact. For example, the third character/digit of "0" in indicia 150 indicates a non-activated status. If indicia 154 is visible in window 22, the third character/digit of "1" in indicia 154 indicates an activated status of indicator 10 and that indicator 10 received an acceleration event in the direction 16. If indicia 152 is visible in window 22, the third character/digit of "2" in indicia 152 indicates an activated status of indicator 10 and that indicator 10 received an acceleration event in the direction 18. Thus, indicator 10 may be configured to indicate both an impact event status and a directional indication of a received impact event. It should be understood that instead of barcode indicia, an alphabetic, numeric, alphanumeric, or other type of enciphered and/or encoded indicia may be used to indicate impact event status and/or a directional indication of a received impact event such that, although the indicia is human-perceptible, the indicia may not be readily interpretable and/or decipherable without a key or other deciphering information. For example, a code indicia such as "SW087654321" in non-barcode form may be used.

Figure 11:
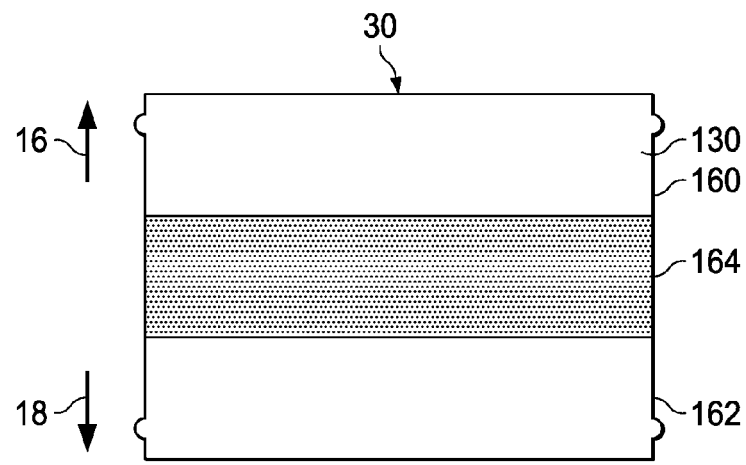
FIG. 11 is a diagram illustrating another embodiment of a mass member for an impact indicator according to the present disclosure.
Figure 12A:
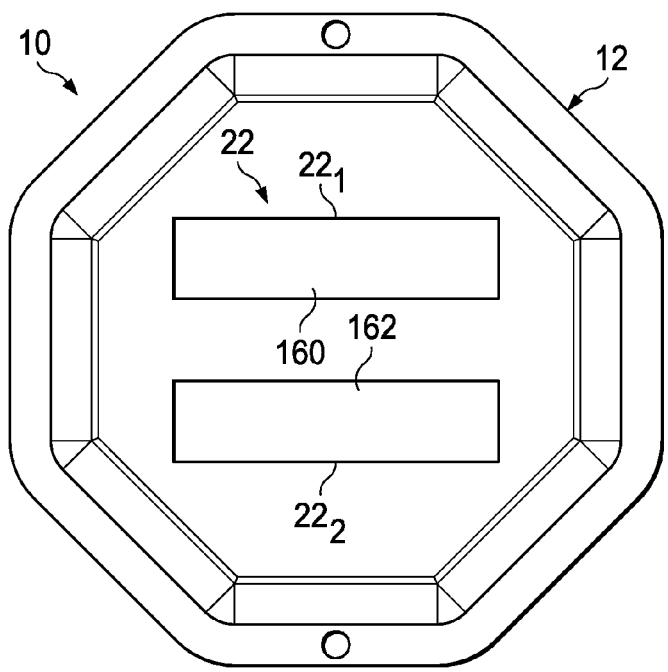
FIGS. 12A and 12B are diagrams illustrating respective non-activated and activated states of an impact indicator with the mass member illustrated in FIG. 11 according to the present disclosure.
Figure 12B:
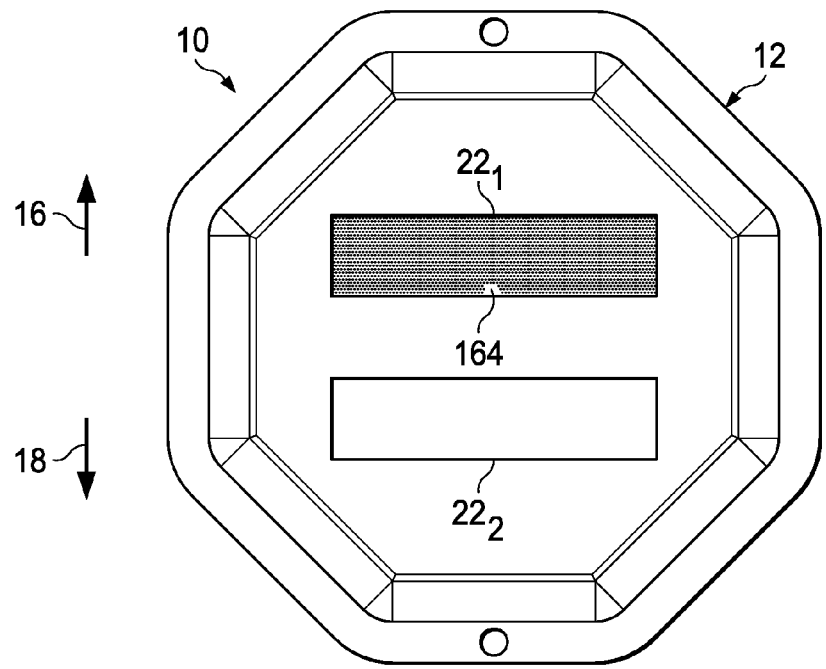

FIG. 11 is a diagram illustrating another embodiment of mass member 30 of indicator 10 in accordance with the present disclosure, and FIGS. 12A and 12B are diagrams illustrating another embodiment of indicator 10 with two status windows 22 (identified as window $22_1$ and $22_2$) utilizing the embodiment of mass member 30 illustrated in FIG. 11. In FIG. 11, surface 130 of mass member 30 comprises non-activated surface portion 160 and 162 and an activated surface portions 164. Surface portions 160, 162 and 164 may comprise different colors, marking or other types of indicia that are visually exposed through windows $22_1$ and/or $22_2$ in either a non-activated or activated state of indicator 10. For example, activated surface portion 164 comprises a surface portion of mass member 30 that will be visible through window $22_1$ when mass member 30 is located in the activated position 96 (FIGS. 2B and 11B) and visible through window $22_2$ when mass member 30 is located in the activated position 116 (FIG. 4A). In a non-activated state (e.g., non-activated position 50 (FIG. 1B)), surface portions 160 and 162 are visible through respective windows $22_1$ and $22_2$. Thus, referring to FIG. 12A, before activation or before being subjected to some predetermined level or magnitude of acceleration event, surface portions 160 and 162 are visible through respective windows $22_1$ and $22_2$. In response to receiving some predetermined level or magnitude of acceleration event, movement of mass member 30 causes surface portion 162 to become visible through one of windows $22_1$ or $22_2$ (depending on the direction of impact event). In FIG. 12B, for example, in response to an impact event in the direction 16, surface portion 164 becomes visible through window $22_1$.

Thus, indicator 10 may be configured in various manners to provide different types of visual indications of activation status. For example, in some embodiments, a color-based display element or display element having barcode or other type of indicia may be provided separate and apart from mass member 30 to provide a visual indication of indicator 10 status via window(s) 22. For example, in some embodiments, spring member 40 and/or 42 may be coupled to another element other than mass member 30 that slides, moves and/or otherwise becomes located within window(s) 22 in response to activation of indicator 10. In another embodiment, spring member 40 and/or 42 may be further coupled to a latch mechanism, pivoting member/element or other type of structure that slides, translates or pivots into an area of window(s) 22 in response to activation of indicator 10. In yet other embodiments, housing 12 may include one or more indicator/display elements located proximate to activated positions 96 and 116 that slide, translate or pivot into an area of window(s) 22 in response to mass member 30 moving into respective activated positions 96 and 116. Indicator 10 may also include a switch or other type of electronic module that causes a visual indication within window(s) 22 in response to indicator 10 activation. For example, in some embodiments, indicator 10 may include a switch, power source and a liquid crystal display (LCD) or other type of electronic display element positioned within window(s) 22 or otherwise located on housing 12 to display a color, barcode or other type of indicia or code indicating an impact detection status, direction of impact and/or other type(s) of information (e.g., manufacturer, serial number, etc.). As an example, indicator 10 may include a switch element located near or at activation position 96 and/or a switch element located near or at activation position 116 that, in response to contact of either switch element by mass member 30, a color, barcode or other type of indicia or code is changed or displayed on the display unit. In this example, using a barcode indicia for example, the display unit may initially display one barcode indicia and electronically change the barcode indicia in response to detecting an impact (including different barcodes based on direction of impact). Thus, it should be understood that a variety of structure and/or methods may be used to indicate impact detection and/or impact direction.

In the embodiment illustrated, for example, in FIGS. 1A, 1B, 2A and 2B, two spring members 40- and 42 are used to retain (at least initially) mass member 30 in a non-activated state or position 50 and to prevent mass member 30 from re-seating in non-activated position 50 after an impact event has caused activation of indicator 10. However, it should be understood that a quantity of spring members may be greater or fewer. For example, in some embodiments, indicator 10 may be configured for unidirectional mass member 30 movement (e.g., in direction 16). In this embodiment, for example, housing 12 may be configured with an additional wall or increased length of mass member 30 such that mass member 30 only moves from non-activated position 50 to activated position 96. In this embodiment, for example, spring member 40 may be omitted while spring member 42 retains the mass member 30 in the non-activated position. In response to an acceleration event in direction 16 of sufficient magnitude to overcome the retention force of spring member 42, mass member 30 moves to the activated position 96, and ends 70 and 82 of leaf spring 58 are drawn out of seats 64 and 76 and into indent regions 102 and 104 (or seats 120 and 122) to thereafter retain mass member 30 in the activated position 96. It should also be understood that the shape and/or configuration of mass member 30 may vary. For example, instead of walls 88 and 90, mass member 30 may comprise posts or other types of surface features to provide a bearing surface against which one or more of spring members 40 and 42 may apply a force.

In some embodiments, spring member 40 and/or 42 is selected and/or otherwise configured to bias and/or otherwise retain mass member 30 in certain positions (e.g., non-activated position 50 and/or activated positions 96/116) until and/or unless a predetermined level or magnitude of impact/acceleration is experienced by indicator 10. For example, impact indicator 10 may be configured for various levels of impact or acceleration activation by setting a particular weight of mass member 30, selecting/configuring a particular thickness and/or material of spring members 40/42, etc. For example, in some embodiments, spring members 40/42 may be configured from a polymer material (e.g., such as a Duralar® material) that may maintain a substantially constant spring tension force over a desired temperature spectrum, thereby alleviating an inadvertent activation of indicator 10 that may otherwise result from a temperature change.

Thus, embodiments of the present disclosure enable impact and/or acceleration event detection while preventing or substantially preventing a re-setting of the state of the impact indicator 10 once a predetermined level or magnitude of impact has occurred. For example, in some embodiments, the mass member 30 of indicator 10 is configured to move from a non-activated position to an activated position in response to an acceleration event. If indicator 10 receives an acceleration event that may be performed in an attempt to re-set indicator 10 to the non-activated state (e.g., a level or magnitude sufficient to cause a reverse movement of mass member 30), the mass member 30 moves from one activated position to another activated position. Further, spring members 40 and/or 42 and/or housing 12 are configured prevent or substantially prevent re-seating of the mass member 30 in the non-activated state or position once indicator 10 has been activated.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

What is claimed is:

1. An impact indicator, comprising:
a housing;
a mass member located within the housing, the housing configured to enable movement of the mass member from a first position to a second position within the housing in response to receipt by the housing of an acceleration event; and
first and second biasing members disposed within the housing and biased toward each other to retain the mass member in the first position, and wherein, in response to receipt by the housing of the acceleration event, the mass member is configured to overcome the biasing force of the first biasing member and move from the first position to the second position, and wherein the first and second biasing members each comprises a leaf spring member having a length greater than a width of the mass member and disposed transversely to a direction of movement of the mass member.

2. The impact indicator of claim 1, wherein, in response to receipt by the housing of the acceleration event, the first and biasing members are biased in a same direction to bear upon the mass member to retain the mass member in the second position.

3. The impact indicator of claim 1, wherein the housing comprises a window to enable a visual indication of movement of the mass member indicating that the housing has experienced the acceleration event.

4. The impact indicator of claim 1, wherein, in response to receipt by the housing of another acceleration event that causes the mass member to overcome the bias of the first and second biasing members, the first and second biasing members are configured to cause the mass member to move from the second position, past the first position, to a third position.

5. The impact indicator of claim 4, wherein the housing comprises a window located in each of the second and third positions to enable a visual indication of the mass member located in either the second or third position.

6. The impact indicator of claim 4, wherein the first and second biasing members are biased in a same direction to bear upon the mass member to retain the mass member in the third position.

7. An impact indicator, comprising:
a housing;
a mass member located within the housing, the housing configured to enable movement of the mass member from a first position to a second position within the housing in response to receipt by the housing of an acceleration event; and
first and second biasing members disposed within the housing and biased toward each other to retain the mass member in the first position, and wherein, in response to receipt by the housing of the acceleration event, the mass member is configured to overcome the biasing force of the first biasing member and move from the first position to the second position; and
wherein the housing comprises a plurality of sidewalls forming a translation path for movement of the mass member from the first position to the second position, and wherein each end of the first and second biasing members is disposed in a respective seat located in the sidewalls when the mass member is in the first position.

8. The impact indicator of claim 7, wherein, in response to receipt by the housing of the acceleration event, the second biasing member is drawn out of its respective seats in the sidewalls and is prevented from returning to its seats in the sidewalls by indents formed in the sidewalls.

9. The impact indicator of claim 7, wherein, in response to receipt by the housing of the acceleration event, the first and second spring members are biased in a same direction to bear upon the mass member to retain the mass member in the second position.

10. The impact indicator of claim 7, wherein, in response to receipt by the housing of another acceleration event that causes the mass member to overcome the bias of the first and second biasing members, the first and second biasing member are configured to cause the mass member to move from the second position, past the first position, to a third position.

11. The impact indicator of claim 10, wherein the housing comprises a window located in each of the second and third positions to enable a visual indication of the mass member located in either the second or third position.

12. The impact indicator of claim 10, wherein the first and second biasing members are biased in a same direction to bear upon the mass member to retain the mass member in the third position.

13. An impact indicator, comprising:
a housing;
a mass member located within the housing, the housing configured to enable movement of the mass member from a first position to a second position within the housing in response to receipt by the housing of an acceleration event; and
first and second biasing members disposed within the housing and biased toward each other to retain the mass member in the first position, and wherein, in response to receipt by the housing of the acceleration event, the mass member is configured to overcome the biasing force of the first biasing member and move from the first position to the second position, and in response to receipt by the housing of the acceleration event, the first and second biasing members are biased in a same direction to bear upon the mass member to retain the mass member in the second position, and wherein, in response to receipt by the housing of another acceleration event that causes the mass member to overcome the bias of the first and second biasing members, the first and second biasing members are configured to cause the mass member to move from the second position, past the first position, to a third position.

14. The impact indicator of claim 13, wherein the housing comprises a window located in each of the second and third positions to enable a visual indication of the mass member located in either the second or third position.

15. The impact indicator of claim 13, wherein the first and second biasing members are biased in a same direction to bear upon the mass member to retain the mass member in the third position.

16. The impact indicator of claim 13, wherein the first biasing member bears against a first wall of the mass member and the second biasing member bears against a second wall of the mass member to retain the mass member in the first position.

17. The impact indicator of claim 16, wherein the first and second walls comprise arcuately formed walls.

18. The impact indicator of claim 16, wherein the first and second walls comprise opposing arcuately formed walls.

19. The impact indicator of claim 13, wherein the first biasing member is configured to invert from a first biasing position to a second biasing position in response to movement of the mass member from the first position within the housing to the second position within the housing.

20. The impact indicator of claim 19, wherein the first biasing member is configured to invert from the second biasing position to a third biasing position in response to movement of the mass member from the second position within the housing to the third position within the housing.

* * * * *